United States Patent [19]

Matta et al.

[11] Patent Number: 5,620,864

[45] Date of Patent: Apr. 15, 1997

[54] ACCEPTOR FOR FUCOSYL TRANSFERASE

[75] Inventors: Khushi L. Matta, Williamsville, N.Y.; E. V. Chandrasekaran, Northbrook, Ill.; Rakesh K. Jain, Palbichla Ajmer, India

[73] Assignee: Health Research, Inc., Buffalo, N.Y.

[21] Appl. No.: 905,797

[22] Filed: Jun. 29, 1992

[51] Int. Cl.$^6$ .............................. C12Q 1/48; C12Q 1/00; G01N 33/48; A61K 38/16

[52] U.S. Cl. .................. 435/15; 435/4; 435/7.1; 435/7.23; 436/63; 436/64; 436/811; 436/813; 436/804; 436/504; 436/518; 536/1.11; 536/4.1; 536/117; 536/123.13; 536/124; 536/55.1; 514/8

[58] Field of Search ..................... 435/15, 810, 7, 435/4, 7.1, 7.23; 436/63, 64, 811, 813, 804, 504; 536/1.11, 4.1, 117, 123.13, 124, 55.1; 514/8

[56] References Cited

U.S. PATENT DOCUMENTS

| | | | |
|---|---|---|---|
| 4,471,057 | 9/1984 | Koprowski et al. | 436/813 |
| 4,675,392 | 6/1987 | Dahmen et al. | 435/15 |
| 4,757,003 | 7/1988 | Matsumoto et al. | 436/813 |
| 4,770,994 | 9/1988 | Rittenhouse | 435/15 |
| 4,971,905 | 11/1990 | Holmes | 435/810 |
| 5,032,505 | 7/1991 | Pierce et al. | 436/64 |
| 5,374,655 | 12/1994 | Kashem et al. | 514/540 |

FOREIGN PATENT DOCUMENTS

WO94/00477  1/1994  WIPO.

OTHER PUBLICATIONS

Hirsch, M.S., "Amer. Jour. of Medicine," vol. 85, pp. 182–185, (1988).
J. Cancer Res. Clin Oncol (1989) 115:451–455. (Yazawa et al).
Cell, vol. 63, 475–484, Nov. 2, 1990.
Clinica Chemica Acta, 201 (1991) 59–64.
Hutchinson et al, Institute of Liver Studies, "Fucosyltransferases: Differential Plasma & Tissue Alterations in Hepatocellular Carcinoma & Cirrhosis" (1990).
"Elevated Activities of Serum α (1 → 3)–L–Fucosyltransferase in Human Cancer", Yazawa et al., Journal of Tumor Marker Oncology, 1989, vol. 4, pp. 355–361.
"Fucosyltransferases: Differential Plasma and Tissue Alterations in Hepatocellular Carcinoma and Cirrhosis", Hutchinson et al., Institute of Liver Studies, Kings College Hospital and School of Medicine and Dentistry, Denmark Hill, London, UK, 1990.
"Changes in Fucose Metabolism Associated with Heavy Drinking and Smoking: A Preliminary Report", Thompson et al., Clinica Chimica Acta, 201: 59–64, (1991).
"Tumor–related Elevation of Serum (α 1 → 3)–L–Fucosyltransferase Activity in Gastric Cancer", Yazawa et al., J. Canc. Res. Clin. Oncol., 115:451–455, 1989.
"Elam–1–Dependent Cell Adhesion to Vascular Endothelium Determined by a Transfected Human Fucosyltransferase cDNA", Lowe et al., Cell, vol. 63, 475–484, Nov. 2, 1990.

*Primary Examiner*—John Kight
*Assistant Examiner*—Louise N. Leary
*Attorney, Agent, or Firm*—Michael L. Dunn

[57] ABSTRACT

A biologically active oligosaccharide compound comprising at least two L hexose rings connected together by an ether oxygen atom. The ether oxygen atom is connected to a first of the rings at the first carbon atom to the right of the hexose ring oxygen atom. The compound contains at least one sulfate or phosphate group connected to the first ring at the third carbon atom to the right of the ring oxygen or to a methyl group at the fifth carbon atom to the right of the ring oxygen atom.

The invention further includes the method for using the above oligosaccharide compound to detect α 1,3-L-fucosyltransferases or to block the activity of such α 1,3-L-fucosyltransferases or structures which mimic the structure of such fucosyltransferases to the extent that such structures bind to compounds of the present invention, e.g., as in the case of HIV virus.

39 Claims, 10 Drawing Sheets

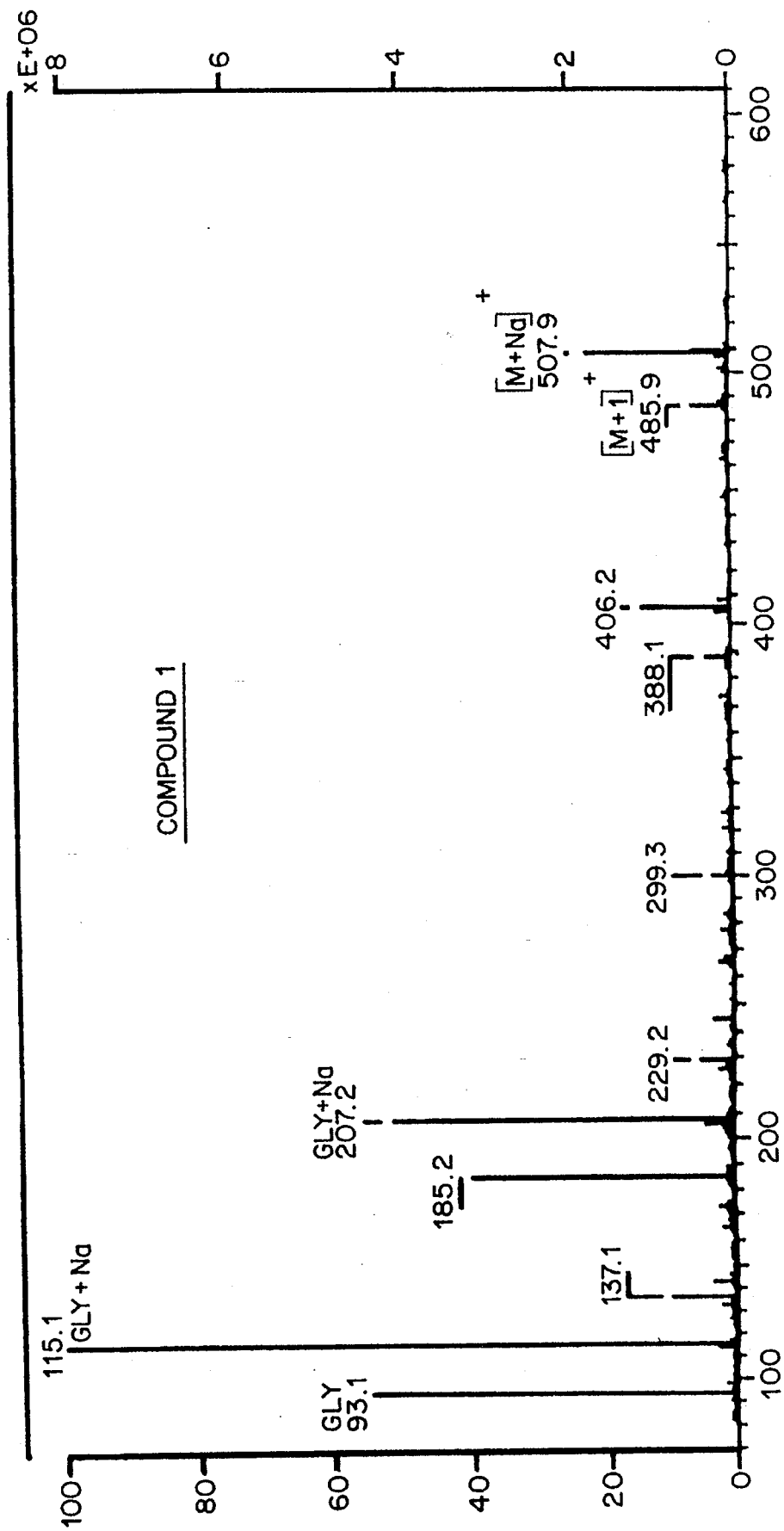

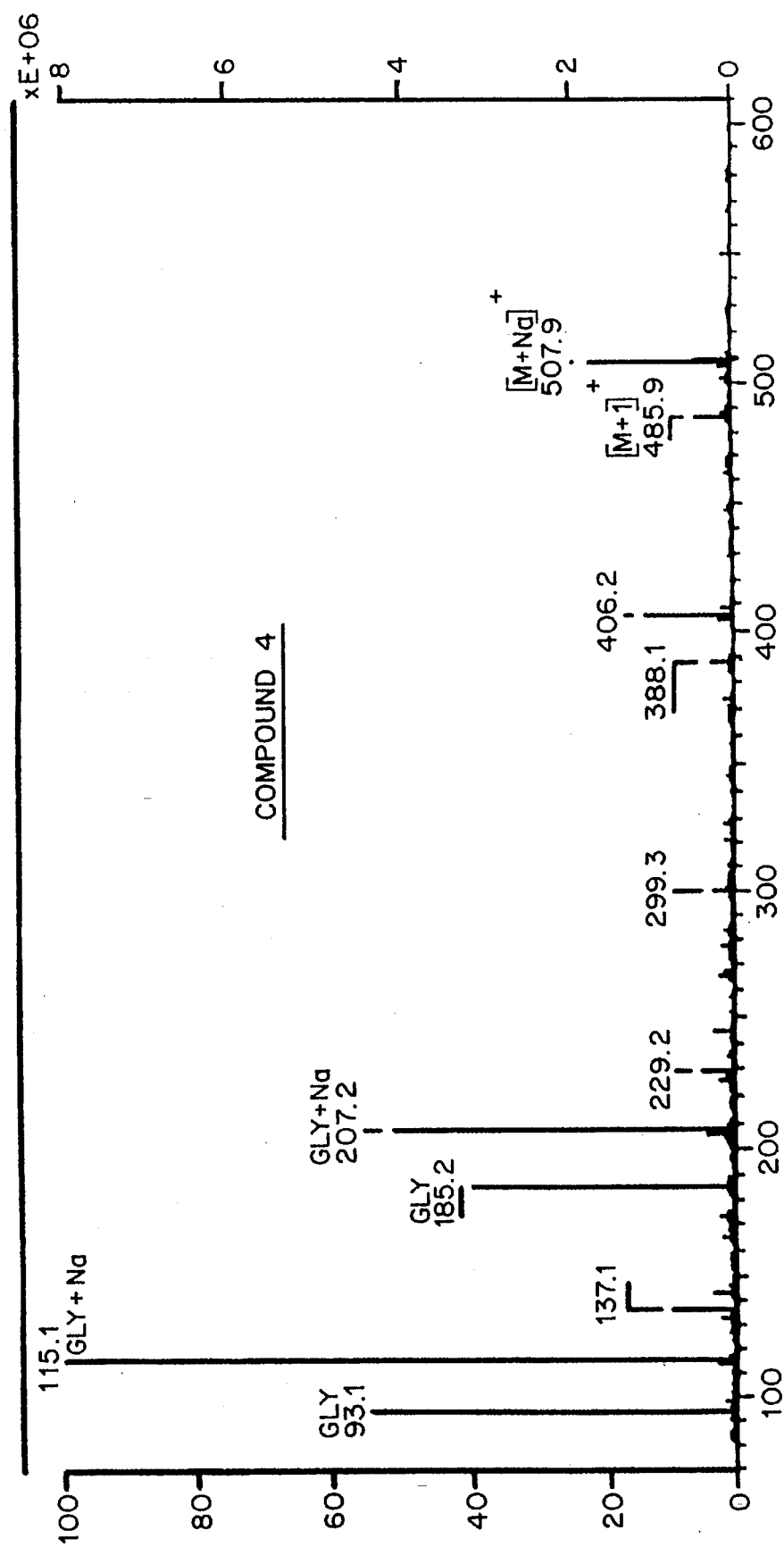
FIG. IC

ACCEPTOR FOR FUCOSYL TRANSFERASE

BACKGROUND OF THE INVENTION

Portions of this invention were made with grants from the National Cancer Institute CA35329 and the National Science Foundation, DMB87-15954. The United States Government may have certain rights in this invention.

α 1,3-L-fucosyltransferases have been found to be elevated in sera of many individuals diagnosed with solid tumors such as those of ovarian cancer, stomach cancer, lung cancer, liver cancer, colon cancer, pancreatic cancer, lingua cancer, and cancer of the larynx and many others. Reference may be had to "Elevated Activities of Serum α (1→3)-L-Fucosyltransferase in Human Cancer", Yazawa et al., Journal of Tumor Marker Oncology, 1989, Vol. 4, No. 4, pp. 355–361 and "Fucosyltransferases: Differential Plasma and Tissue Alterations in Hepatocellular Carcinoma and Cirrhosis", Hutchinson et al , Institute of Liver Studies, Kings College Hospital and School of Medicine and Dentistry, Denmark Hill, London, UK, 1990 and "Changes in Fucose Metabolism Associated with Heavy Drinking and Smoking: A Preliminary Report", Thompson et al , Clinica Chimica Acta, 201: 59–64 (1991); and "Tumor-related Elevation of Serum (α1→3)-L-Fucosyltransferase Activity in Gastric Cancer", Yazawa et al , J. Canc. Res. Clin. Oncol., 115: 451–455, 1989; all of which are incorporated herein by reference. This enzyme thus appears useful as a diagnostic marker for cancer.

The expression of mono, di and trimeric x-determinants in glycolipids of colon carcinoma was shown to be due to the retrogenetic expression of type 2 chain precursors (Galβ1, 4 Glc NAcβ) that were not found in normal adult colonic epithelial cells. This implies that the type of the precursor restricted the fucosyltransferase involved to transfer fucose to the C-3 position of GlcNAc. Further, human colonic adenocarcinoma Colo 205 cells, in contrast to human small cell lung carcinoma NCI-H69 cells and lung carcinoma PC 9 cells (9,10), transferred fucose in α1,4 linkage to lacto-series type 1 chain structures (Gal β1,3 Glc NAcβ) and in α1,3 linkage to type 2 chain structures. A report on the separation of α1,3 and α1,4 fucosyltransferase activities of human milk on Sephacryl S-200 column indicated that neither enzyme fraction was absolutely specific for type 1 or 2 chain acceptors. It becomes thus evident that the expression of α1,3 and α1,4 fucosylated lacto-series carbohydrate chains involves fucosyltransferases exhibiting varying degrees of substrate specificity and differing cell and tissue distribution (14–16). Carbohydrates containing the type 2 chain Galβ1, 4GlcNAcβ and the corresponding NeuAcα2, 3Galβ1, 4GlcNAcβ-type structures have been used for the assay of α1,3-L-fucosyltransferases. It has been shown that 2'-fucosyl LacNAc is a preferred substrate for α1,3-L-fucosyltransferase of human neuroblastoma cells. Apart from the known sulfated glycoconjugates such as mucins and glycolipids, sulfate groups have only recently been identified in some glycoproteins. The sulfate group in glycolipids is generally linked to a position, otherwise occupied by a sialyl residue. It has been found that SO$_4$→3Galβ1, 4GlcNAc is a terminal sequence of the asparagine linked carbohydrate chain of porcine thyroglobulin.

Adhesion of circulating leukocytes to the vascular endothelium during inflammation is mediated in part by their interaction with the endothelial-leukocyte adhesion molecule ELAM-1, a member of the LELAM family of adhesion molecules, and there is evidence that the interactions may be regulated by certain α(1–3) fucosyltransferases. See "ELAM-1-Dependent Cell Adhesion to Vascular Endothelium Determined by a Transfected Human Fucosyltransferase cDNA", Lowe et al., Cell, Vol. 63, 475–484, Nov. 2, 1990.

It is therefore desirable to have a compound which will bind to α 1,3-L-fucosyltransferases with sufficient specificity so that the α 1,3-L-fucosyltransferases can be easily selectively detected both for purposes of investigation and for purposes of diagnoses and predication of disease. Further, such a binding compound can affect the activity of α 1,3-L-fucosyltransferases thus desirably slowing or stopping diseases in which it is implicated. Such a binding compound can further bind to organic structures which mimic the structure of α1,3-L-fucosyltransferases, at least insofar as binding sites are concerned.

Further, such a binding compound may be attached to auxiliary compound structures such as toxins or antineoplastic compounds to carry such auxiliary structures to the α 1,3-L-fucosyltransferases or organic structures which mimic them.

A number of acceptors for fucosyltransferases are known, unfortunately such acceptors do not distinguish α 1,3-L-fucosyltransferases from other fucosyltransferases as well as desired. Such acceptors are also not as sensitive as desired and do not have an affinity as high as desired.

Examples of compounds which, to a more or less extent, may act as acceptors for fucosyltransferases are 2'methyl lactosamine (2'methyl Lac NAc), 2'-fucosyl Lac NAc, 3-fucosyl Lac NAc, and the β-benzyl glycosides of Lac NAc, 2'methyl Lac NAc, Galβ1 and 3 GalNAc.

BRIEF DESCRIPTION OF THE INVENTION

In accordance with the invention there is therefore provided an oligosaccharide compound which will bind to α 1,3-L-fucosyltransferases.

More particularly, the compound comprises a biologically active oligosaccharide compound comprising at least two L hexose rings connected together by an ether oxygen atom. The ether oxygen atom is connected to a first of the rings at the first carbon atom to the right of the hexose ring oxygen atom. The compound contains at least one sulfate or phosphate group connected to the first ring at the third carbon atom to the right of the ring oxygen or to a methyl group at the fifth carbon atom to the right of the ring oxygen atom.

The invention further includes the method for using the above oligosaccharide compound to detect α 1,3-L-fucosyltransferases or to block the activity of such α 1,3-L-fucosyltransferases or structures which mimic the structure of such fucosyltransferases to the extent that such structures bind to compounds of the present invention, e.g., as in the case of HIV virus.

In particular embodiments of the invention, the oligosaccharide may be represented by the formula:

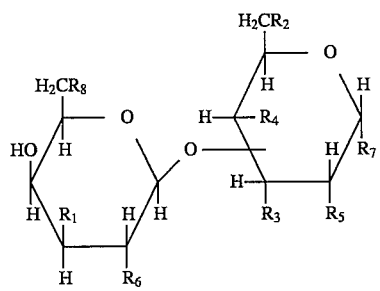

wherein at least one of $R_1$ and $R_2$ is sulfate or phosphate, one of $R_3$ and $R_4$ represents the link to the linking oxygen atom and the remaining R groups are selected from —OH, —OR$_9$ or —R$_{10}$ where $R_9$ and $R_{10}$ are independently selected from the group consisting of lower alkyl, lower alkenyl, allyl, phenyl, benzyl, monosaccharides, oligosaccharides, toxins, antibodies, enzymes, amino acids and amino acid chains and wherein $R_{10}$ may further be ester, ether, amino or fluoro; provided that, at least three of the remaining R groups are —OH.

BRIEF DESCRIPTION OF THE DRAWINGS

FIGS. 1A and 1B show fast bombardment ionization spectra of compound 1.

FIGS. 1C and 1D show fast bombardment ionization spectra of compound 4.

Ovarian tumor α 1,3-L-fucosyltransferase preparation, which was obtained from affinity chromatography on bovine IgG glycopep-Sepharose (sample volume: 2.0 ml) was applied to Sephacryl S-200 column (2.6 cm×88.0 cm) equilibrated in the cold room with 50mM Tris-HCl, pH 7.0 containing 0.15M NaCl, 0.1% Triton X-100. Fractions of 3.0 ml were collected at a flow rate of 9.0 ml per h. The fucosyltransferase was assayed with the acceptor, 2' fucosyl LacNAc.

Figure 4:
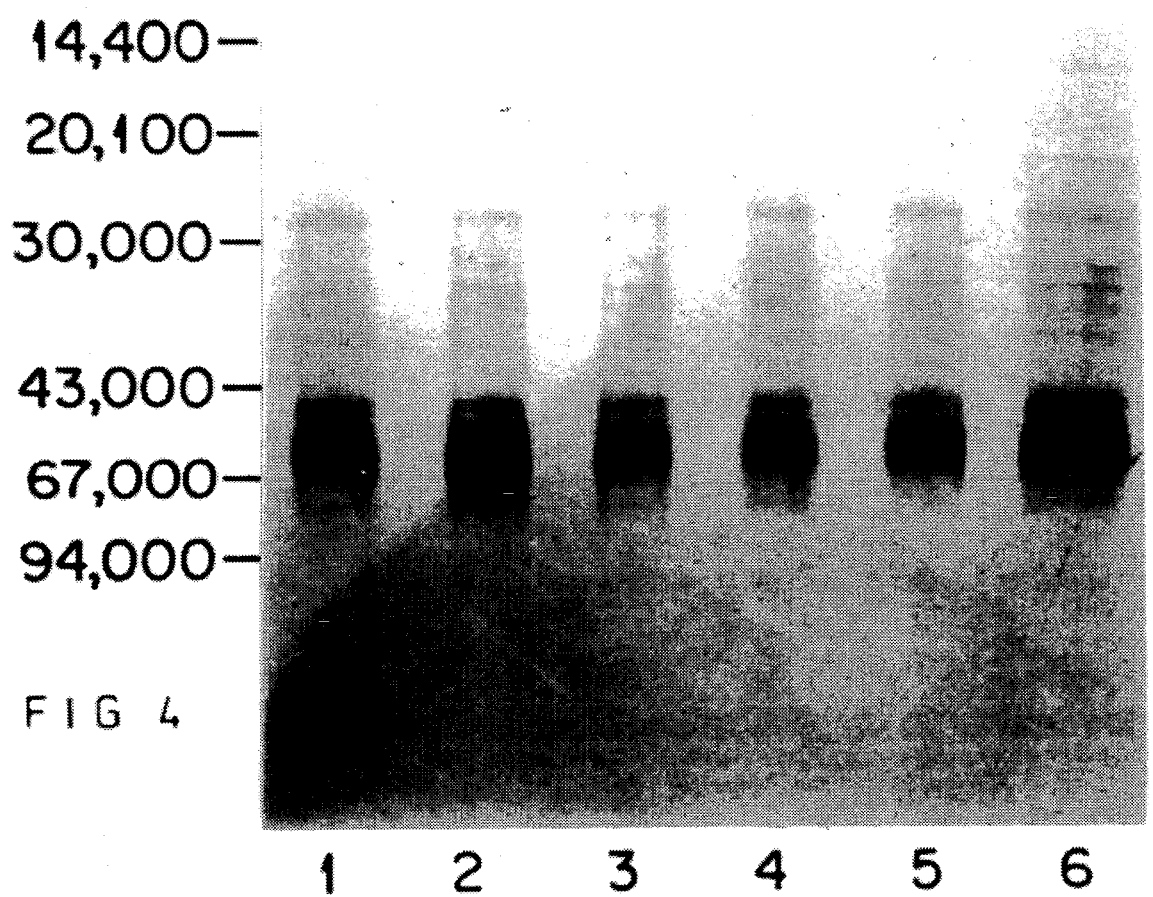

FIG. 4 SDS-PAGE (Phast Gel 8–25, Pharmacia System) purified from the soluble fraction of human ovarian tumor: Lanes 1→5: 1 μg of the enzyme protein was applied; Lane 6: 2 μg of the enzyme protein. The gel was stained with Coomassie blue.

Figure 5:
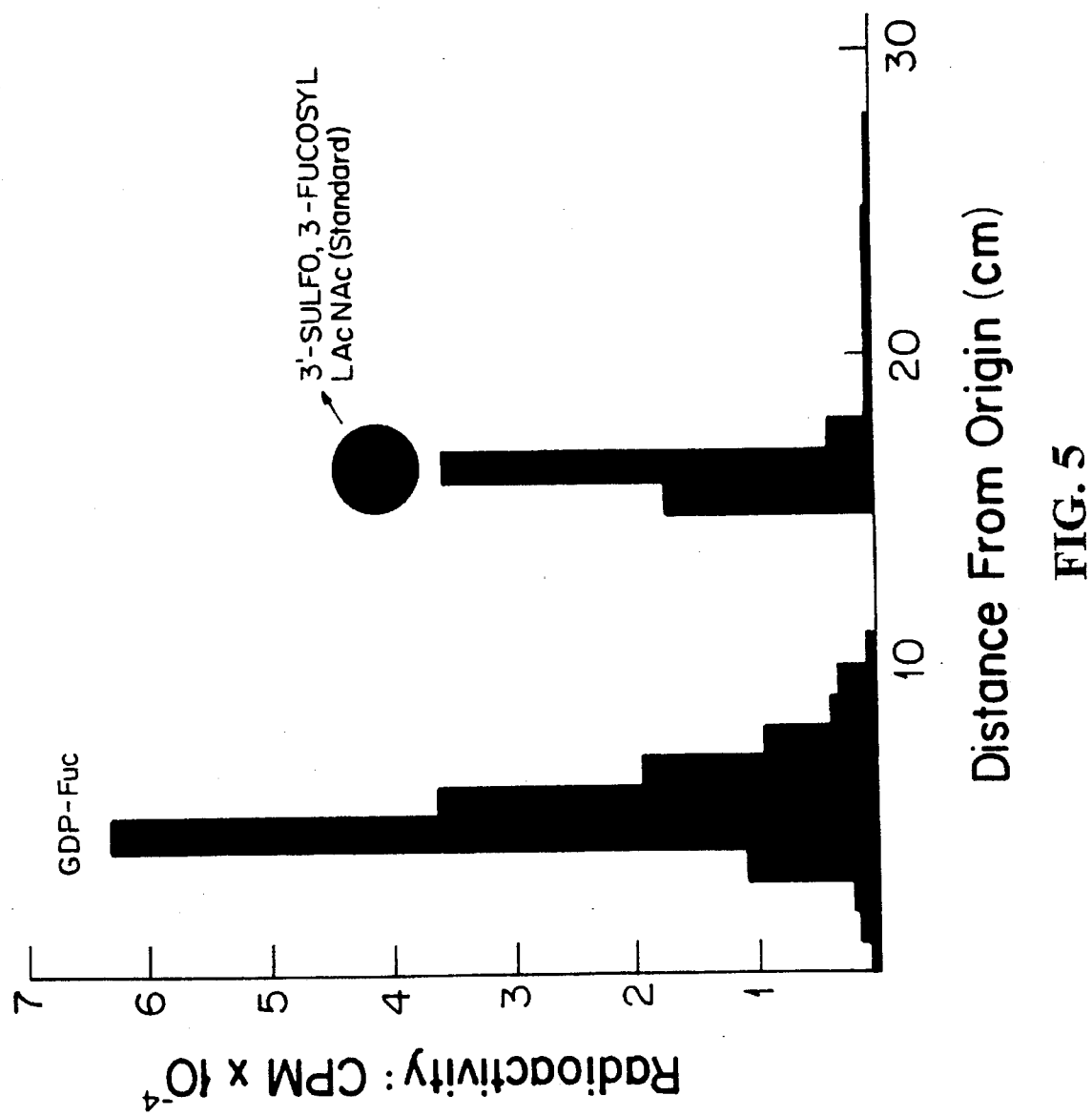

FIG. 5 Paper chromatography of the [$^{14}$C] fucosylated product arising from the incubation of 3'-sulfo LacNAc with serum α1,3-L-fucosyltransferase. For details, see text.

DETAILED DESCRIPTION OF THE INVENTION

"Oligosaccharide, as used herein, means a plurality of hexose and pentose rings connected together, usually by one or more ether oxygen atoms.

The most preferred oligosaccharides of the invention are hexose disaccharides which are usually lactose derivatives.

The compounds may be named by reference to carbon atom number in the oligosaccharide which for example, in the case of lactose derivatives are numbered as shown in the following structural formula:

```
       6'                    6
     HOCH2                 HOCH2
       |  O                   |  O
     /5'  \                 /5  \
    /4'    1'\ — O — /4    1\
    \3' 2'  /          \3  2/
       |                    |
```

Several preferred compositions of the invention may therefore be named:
1 sodium 3'-0-sulfo-2N-acetyllactosamine β1→0 benzyl and
2 sodium 6-0-sulfo-2N-acetyllactosamine β1→0 benzyl and where the ether oxygen is connected to the 3 carbon atom instead of the 4 carbon atom:
3 sodium 3'-0-sulfo-lacto-2N biose I β1–0 benzyl and
4 sodium 6-0-sulfo-lacto-2N biose I β1–0 benzyl.

Higher polysaccharides are contemplated in accordance with the invention, e.g., where each ring is numbered separately each having carbon atoms 1 through 6 compounds 1 and 3 above may be named as Benzyl 4-0-(sodium β-D-Galactopyranosyl 3-Sulfate)-2-acetamido-2-deoxy-β-D-Glucopyranoside and Benzyl 3-0-(sodium β-D-Galactopyranosy 3-Sulfate)-2-acetamido-2-deoxy-β-D-Glucopyranoside.

Unexpectedly, the presence of the sulfate or phosphate group at the 3' or 6 carbon atom renders the compound selective for 1,3-L-fucosyltransferase.

Essentially, any other functional group may be added to the saccharide rings provided that such groups do not seriously chemically or physically hinder the binding properties of the compounds of the invention to the desired 1,3-L fucosyl transferase.

Such substitutions may be made at the $R_1$–$R_8$ groups as shown in the formula set forth in the brief description of the invention. Such substitutions are made either by replacement of an entire —OH group, e.g., by substitution by an amine or fluoride group, or by replacement of the hydrogen atom in a hydroxy group e.g., by ester or ether formation or by substitution into an aromatic ring.

The $R_1$–$R_8$ groups may be —OH, —OR$_9$ or —R$_{10}$ where $R_9$ and $R_{10}$ are independently lower alkyl, lower alkenyl, allyl, phenyl, benzyl, monosaccharides, oligosaccharide, toxins, antibodies, enzymes, amino acids and amino acid chains including peptides and proteins and $R_{10}$ may further be fluoro or ester, ether or amino groups which may further link saccharides, amino acids, amino acid chain enzymes, antibodies and toxins.

Usually, to prevent hinderance, at least three and usually four of $R_1$–$R_8$ are —OH groups.

It is to be understood that any of the above groups may be further substituted, e.g., with one or more of lower alkyl groups, —OH groups, ether groups, ester groups, carboxy groups, amino groups, fluoro groups, saccharides, antibodies, toxins, enzymes, radioisotopes, and nucleic acids.

Antibodies can be joined to the base oligosaccharide by methods known to those skilled in the art, e.g., as described in Fitzgerald et al., Proc. Natl. Acad. Sci. USA, Vol. 84, pp. 4288–4292, June 1987. Antibodies which can be joined are of many types including polyclonal and monoclonal antibodies.

Toxins which can be joined include such structures as the Ricin A chain fragment. Procedures for attachment of the Ricin A chain are well known to those skilled in the art, e.g., by covalent bonding. Other toxins or drugs which may be attached may include cytotoxic agents such as methotrexate.

Other enzymes, some of which may have hormone like activity, which may be attached include biological response modifiers such as interleukins, interferons and growth factors and may include phosphase type enzymes.

Radioisotopes and nucleic acids and derivatives may be attached by known methods.

Particularly desirable R groups, e.g., at the $R_7$ position are aromatics such as benzyl and nitrophenyl since they have a distinctive NMR resonance pattern which assists detection. The $R_5$ and $R_7$ groups, being distally removed from the area believed to be reactive with 1-3-L fucosyltransferases, are particularly suitable, often through ester, ether or amino linkages, to larger groups such as additional saccharide rings and peptide chains.

Examples of saccharides which may be attached as the $R_5$ and $R_7$ groups, usually through an ether link are glucose, fructose, aldose, mannose, ribose and galactose.

The compounds of the invention may be used to detect for the presence and to quantify α 1,3-L-fucosyltransferase. This can be easily and readily accomplished by incubating a compound of the invention with a sample containing α 1-3-L fucosyltransferase as described subsequently with respect to the specific examples.

Several derivatives of Lac NAc were synthesized and tested for their ability to act as acceptors for α 1,3-L-fucosyltransferase present in sera of patients having ovarian cancer and in human ovarian tumor particulate and soluble fractions. These compounds were 3'sulfo LacNAc, 6'-sulfo LacNAc, 6-sulfo LacNAc, and the β benzyl glycoside of 3'-sulfo LacNAc.

These compounds were compared with 2'-methyl LacNAc as a standard, a compound known to have acceptor properties for numerous fucosyltransferases.

In the comparisons, the activities were based upon the ability of 2' methyl LacNAc to act as an acceptor at a base value of 100%.

As compared with 2' methyl LacNAc, 3'-sulfo LacNAc was about 3 to 5 fold more sensitive in measuring enzyme level of α 1,3-L-fucosyltransferases in blood sera than 2' methyl LacNAc. The serum enzyme also had a very high affinity (Km) for 3'-sulfo LacNAc. Using competitive analysis Km for 3'-sulfo LacNAc in the presence of 3.0 mM of 2'-methyl LacNAc was 0.12 mM and that for 2' methyl LacNAc in the presence of 0.3 mM of 3'-sulfo LacNAc was 6.67 mM. The lower the number, the greater the affinity, thus 3'-sulfo LacNAc has a much greater affinity for the enzymes than 2' methyl LacNAc.

More specifically, when ovarian cancer sera was used as the enzyme source, the sulfate group at C-3 of LacNAc enhanced the acceptor ability (sensitivity) to 341% compared to 2' methyl LacNAc at 100% standard. By comparison, a sulfate group at C-2' or C-6' decreased the activity of 22% and 36% respectively. The sulfate group at C-6 increased the activity to 172% compared to 2' methyl LacNAc at 100%

The β benzylation at C-1 2' methyl LacNAc increased the activity of LacNAc and two to three times but decreased the activity of 3'-sulfo LacNAc.

The enzymes of the soluble tumor fraction was partially purified (16 fold at 39% yield) by affinity chromatography on bovine IgG glycopeptide-sepharose. Further purification to apparent homogeneity, as shown by sodium dodecyl sulfate-polyacrylamide gel electrophoresis (Mr=<67,000) was achieved by Sephacryl S-200 chromatography (66 fold, 6% yield). The fucosyltransferase enzyme mixture, at complete purification, is unstable.

The enzyme mixture of the soluble fraction exhibited even greater activity than the serum fraction towards 3'-sulfo LacNAc, 447% and 272% for 6-sulfo LacNAc, as compared with 2' methyl LacNAc at 100%. By contrast 2' sulfo LacNAc and 6' sulfo LacNAc only show 33% and 5% activity respectively.

The enzyme mixture of soluble tumor is also very active with Galβ1, 3 GlcNAc (566%), the β-benzyl glycosides of Galβ1, 3 Glc NAc (1005%) and 3-sulfoGalβ1, 3 GlcNAc (415%) indicating the coexistence of α 1,3 and α 1,4 fucosyltransferase in this mixture.

EXAMPLES

Sera were collected from healthy females and ovarian cancer patients admitted to Roswell Park Cancer Institute in Buffalo, N.Y., USA. Ovarian tumor tissues were obtained during surgical procedures from patients with ovarian cancer. Both sera and tissues were stored frozen at −70° C. until use.

Isolation of glycopeptides from bovine IgG by pronase digestion, gel filtration and Con-A-Sephorose chromatography and then coupling to Sepharose 4 β was performed as described by Foster, C. S. et al., (1991) J. Biol. Chem. 226, 3526–3531.

This affinity matrix (30 ml in bed volume) was washed and equilibrated at 4° C. with 25 mM Tris-HCl pH 7.0 containing 35 mM $MgCl_2$, 10 mM $NaN_3$ and 1 mM ATP.

Paper chromatographic identification of the [$^{14}$C] fucose containing product arising from 3'-sulfo LacNAc incubation mixture (100 μl) was spotted on a Whatman 3 MM chromatographic paper and subjected to chromatography in ethyl acetate/pyridine/water:12/5/4 for 48 hours. The chemically synthesized product 3'-sulfo 3-fucosyl LacNAc was also run in parallel on the paper. The radioactivity was located on the paper by cutting 1 cm sections, soaking them in 1 ml water in vials and detecting the radioactivity by scintillation counting. The non-radioactive standard was located on the paper by alkaline silver reagent. Protein was assayed by the BioRad micromethod with BSA as the standard. Protein in the presence of Triton X-100 was determined by a modified Lowry procedure (Trevelyn et al. (1950) Nature (Lond.) 166, 444–445).

Assay of α1,3-FUCOSYLTRANSFERASE

An incubation mixture contained 50 mM HEPES-NaOH, pH 7.5, 5 mM $MnCl_2$, 7 mM ATP, 3 mM $NaN_3$, the acceptor 0.3 mM (for serum enzyme) or 3.0 mM (for tumor enzyme), 0.125 μCi of GDP-[U-$^{14}$C] Fuc (Sp. Act. 216 mCi/mmol) and enzyme in a total volume of 0.10 ml; the control incubation mixture had everything except the acceptor. At the end of incubation at 37° C. for 18 h, the mixture was diluted with 1 ml water and passed through Dowex-1-C1 column (1 ml in a Pasteur pipet). The column was washed twice with 1 ml water; the breakthrough and wash, which contained the [$^{14}$C] fucosylated neutral acceptor, were collected together in a scintillation vial and counted for radioactivity using the scintillation coctail 3a70 (Research Products International, Mount Prospects, Ill.) and Beckman LS9000. The Dowex column was then eluted successively with 3 ml each of 0.1M and 0.2M NaCl; these eluates which contained the [$^{14}$C] fucosylated sulfated acceptors, were counted for radioactivity as before. Corrections were made by subtracting the radioactivity in the water and NaCl eluates of the control incubation mixture from the corresponding test fractions. The duplicate runs of samples gave almost identical values, the difference being <5%.

Chemical Synthesis:

β-D-GALACTOPYRANOSYL-(1→4)-SODIUM 2-ACETAMIDO-2-DEOXY-D-GLUCOPYRANOSE 6-SULFATE (Compound 1)

Glycosylation of benzyl-2-acetamido-3-O-benzyl-2-deoxy-6-O-(4-methoxybenzyl)-α-D-glucopyranoside with 2,3,4,6- tetra -O-acetyl-α-D-galactosyl bromide afforded the fully protected disaccharide. The selective removal of 4-methoxybenzyl group with DDQ in dichloromethane provided the alcohol (compound 2). Reaction of 2 with five molar equivalents of sulfur trioxide-pyridine complex in N,N-dimethylformamide produced 3 as its sodium salt after cation ($Na^+$) exchange. O-Deacetylation of 3 in methanolic sodium methoxide, followed by hydrogenolysis of the benzyl group in the presence of palladium-on-carbon furnished Compound 1 as an amorphous solid after passage through a cation ($Na^+$)—exchange resin column. $[α]_D$+26.5 (c 1.3, water); For $^{13}$C-n.m.r. and m/z data, see Table I.

SODIUM β-D-GALACTOPYRANOSYL 3-SULFATE-(1→4)-2-ACETAMIDO-2-DEOXY-D-GLUCOPYRANOSE (Compound 4)

The reaction of benzyl 2-acetamido-2-deoxy-3,6-di-O-benzyl-4-O-(4,6-O-benzylidene-2-O-benzyl-β-D-galactopyranosyl)-α-D-glucopyranoside in N,N-dimethyl formamide with $SO_3$-pyridine complex at room temperature afforded the corresponding 3'-O-sulfo derivative which on hydrogenolysis followed by purification over Dowex-1 (acetate form) column and treatment with $Na^+$ resin yielded compound 4 as an amorphous solid. $[\alpha]_D+21.3$ (C 0.5, $H_2O$). For $^{13}$C-n.m.r. and m/z data see Table I.

O-α-L-FUCOPYRANOSYL-(1→3)-[SODIUM O-β-D-GALACTOPYRANOSYL 3-SULFATE-(1→4) ]-2-ACETAMIDO-2-DEOXY-D-GLUCOPYRANOSE (Compound 5)

Glycosylation of benzyl 2-acetamido-4-O-(2,3,4,6-tetra-O-acetyl-β-D-galactopyranosyl)-6-O-benzyl-2-deoxy-α-D-glucopyranoside with methyl 2,3,4-tri-O-benzyl-1-thio-β-L-fucopyranoside, in the presence of cupric bromide-tetrabutyl ammonium bromide, followed by O-deacetylation with methanolic sodium methoxide afforded known benzyl 2-acetamido-6-O-benzyl-3-O-(2,3,4-tri-O-benzyl-α-L-fucopyranosyl-4-O-(β-D-galactopyranosyl)-2-deoxy-α-D-glucopyranoside (compound 6). Isopropylidenation of 6 by the procedure of Catelani et al. afforded 3',4'-O-acetyl derivative (compound 7); $[\alpha]_D+21$ (c 0.9, $CHCl_3$); $^1$H-n.m.r. ($CDCl_3$): δ7.42–7.16 (m, 25 H, arom.), 1.50 (s, 3 H, NAc), 1.45 and 1.25 (each s, 3 H, $CMe_2$), 1.13 (d, J~6 Hz, 3 H, CMe). Acetylation of 7 with pyridine-acetic anhydride and followed by cleavage of the isopropylidene group with 80% aqueous acetic acid gave the diol: $[\alpha]_D+5.75$ (c 0.8, $CHCl_3$); $^1$ H-n.m.r. ($CDCl_3$): δ7.45–7.10 (m, 25 H, arom.), 2.03 (s, 3 H, OAc), 1.98 (s, 3 H, OAc), 1.54 (s, 3 H, NAc), 1.17 (d, J 6 Hz, 3 H, CMe). This was converted into its 3',4'-(ethyl ortho acetate) which was hydrolyzed with 80% aqueous acetic acid to give 3'-hydroxy key intermediate 8; $[\alpha]_D+10.4$ (c 0.5, $CHCl_3$); $^1$ H-n.m.r. ($CDCl_3$): δ7.38–7.08 (m, 25 H, arom.), 2.01 (s, 6 H, 2×OAc), 1.91 (s, 3 H, OAc), 1.51 (s, 3 H, NAc), 1.17 (d, J~6 Hz, 3 H, CMe). Sulfation of 8 in a manner analogous to that described for 2 (to give 3, gave 9 as its sodium salt. O-Deacetylation of 9 in methanolic sodium methoxide, followed by removal of the benzyl ether protecting groups afforded the sodium salt of O-α-L-fucopyranosyl-(1→3)-[O-β-D-galactopyranosyl 3-sulfate-(1→4)]-2-acetamido-2- deoxy-D-glucopyranose (5) after purification over Dowex-1 (acetate form) column followed by treatment with cation-($na^+$) exchange resin; $[\alpha]_D$_10.7 (initial) →–8.9 (after 72 h). (C 0.3, $H_2O$); for $^{13}$C-n.m.r. and m/z data, see Table I. Hydrogenolysis of the benzyl groups of 6, followed by column chromatographic purification on silica gel gave known free trisaccharide 10; for $^{13}$C-n.m.r. and m/z data see Table I. The chemical synthesis of other compounds used in the present study is communicated elsewhere.

The purity of the synthetic sulfated compounds 1, 4 and 5 were checked by thin layer chromatography on silica gel as well as on cellulose plates and also by paper chromatography. Their structural assignments were confirmed by $^{13}$C-n.m.r. (Table I) and f.a.b. mass spectroscopy (FIGS. 1A–1F).

In the $^{13}$C spectrum of 1, the resonance for C-6 of the 2-acetamido-2-deoxy-D-glucose (GLcNAc) residue suffered a downfield shift of 6.3 p.p.m., by comparison to that of its counterpart in the spectrum of compound 4, evidencing that 0–6 was the site of sulfation. However, in the spectra of both 4 and 5, analogous downfield shift of 7.6 p.p.m. and 7.7 p.p.m., respectively, were observed for C-3 resonances of their corresponding Gal residues, confirming that sulfation had occurred at 0–3' in both the compounds.

Figure 1B:
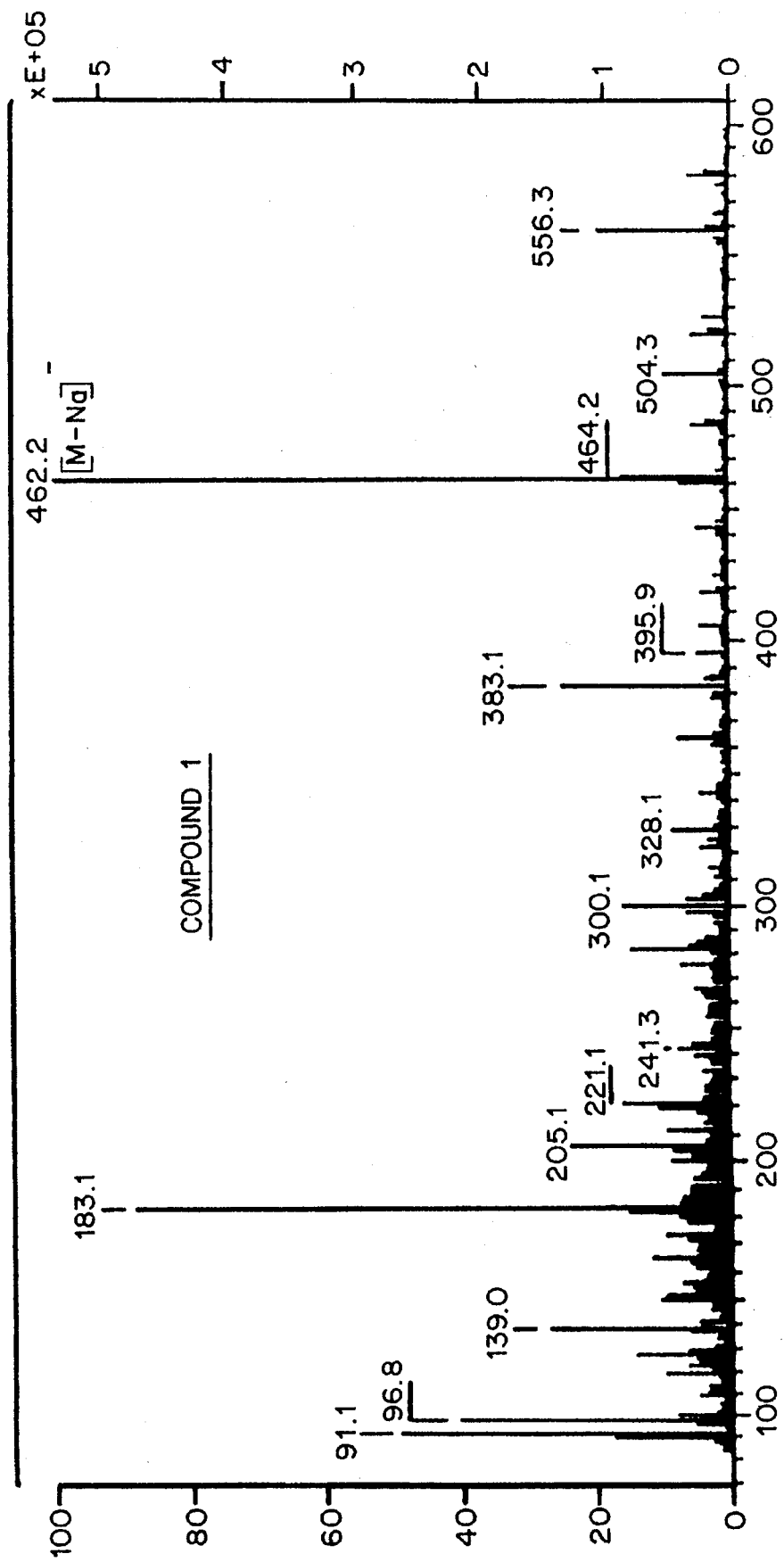
Figure 1D:
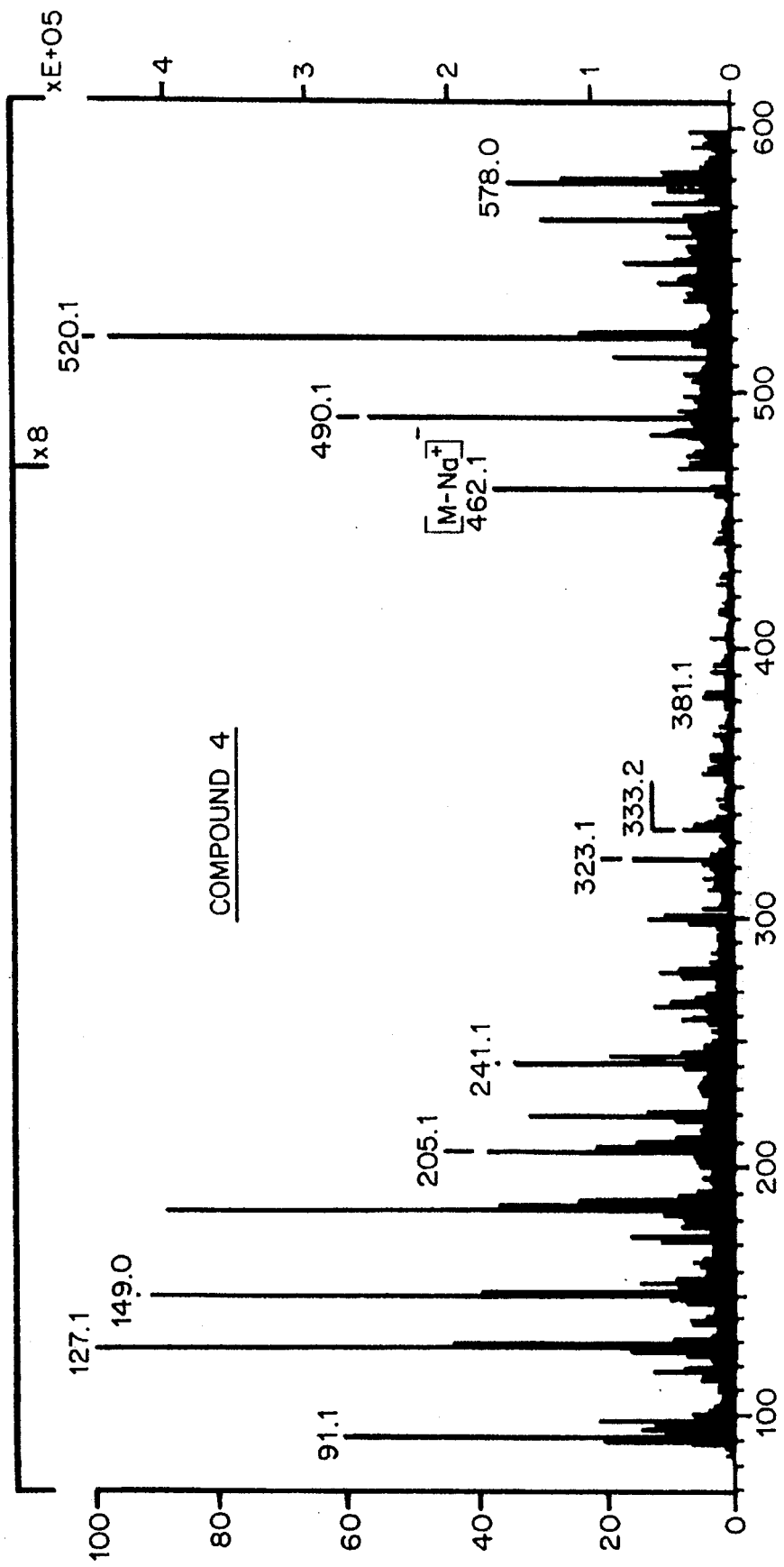
Figure 1E:
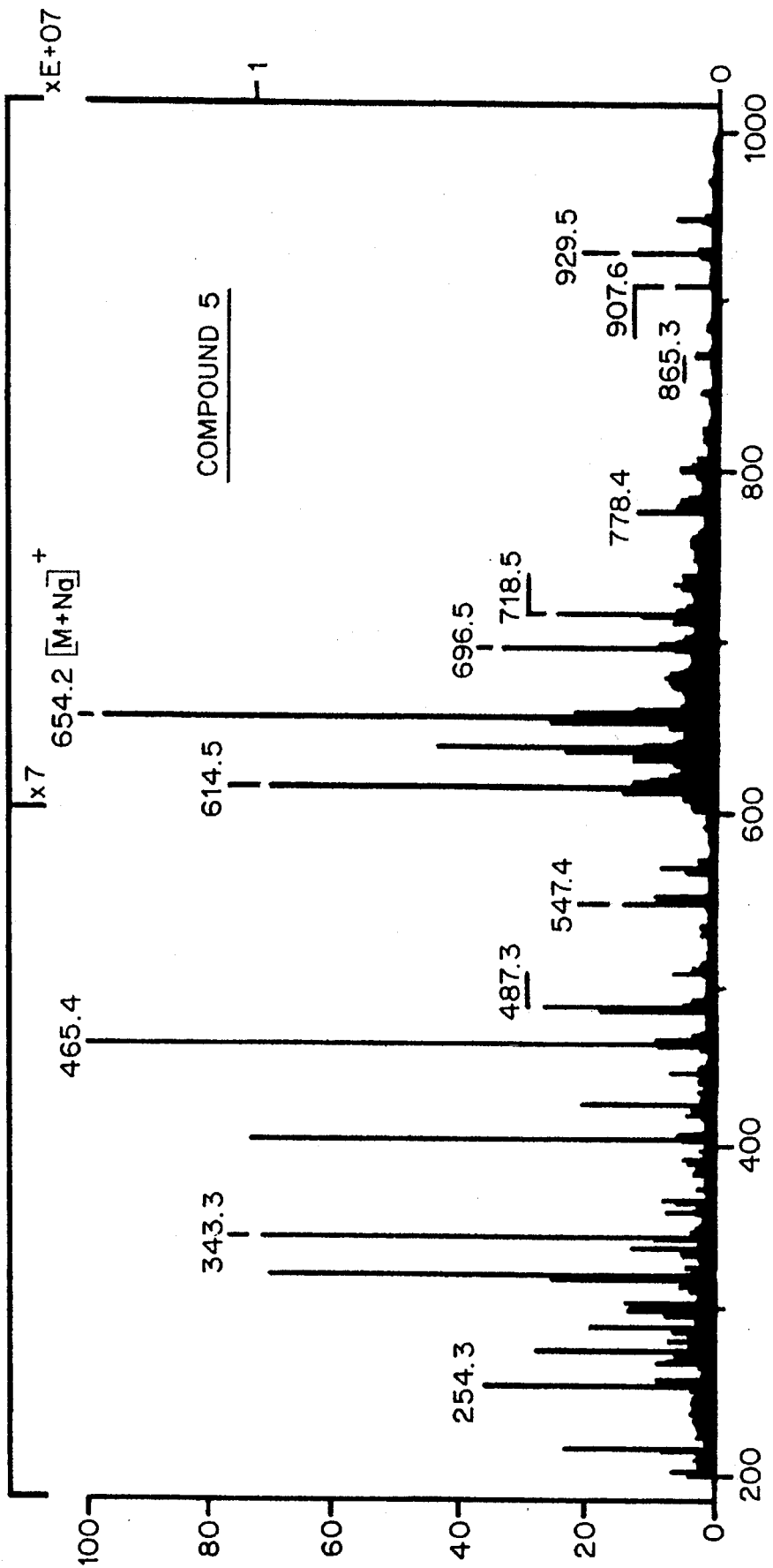
FIGS. 1E and 1F show fast bombardment ionization spectra of compound 5.
Figure 1F:
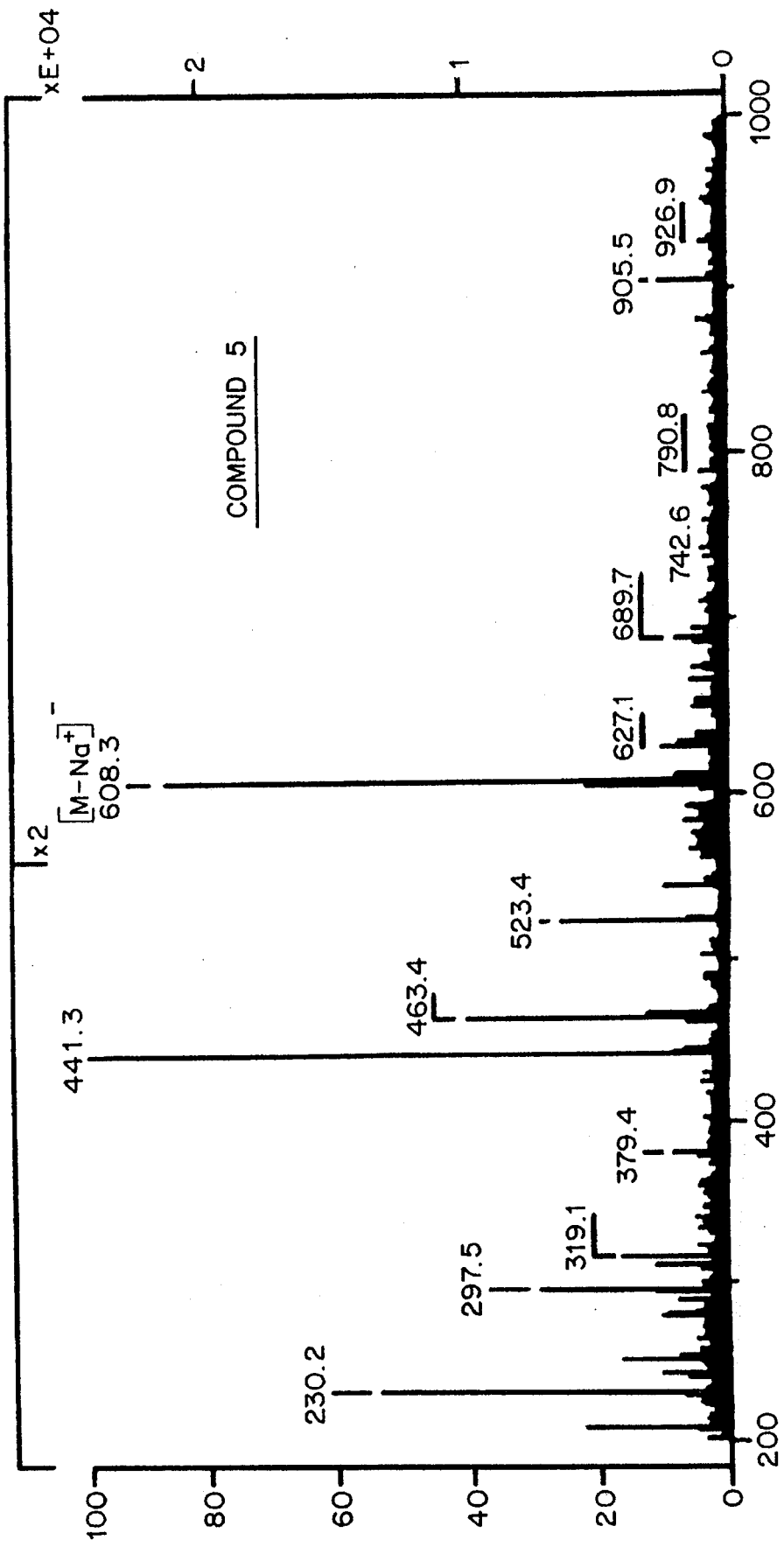
Figure 2:
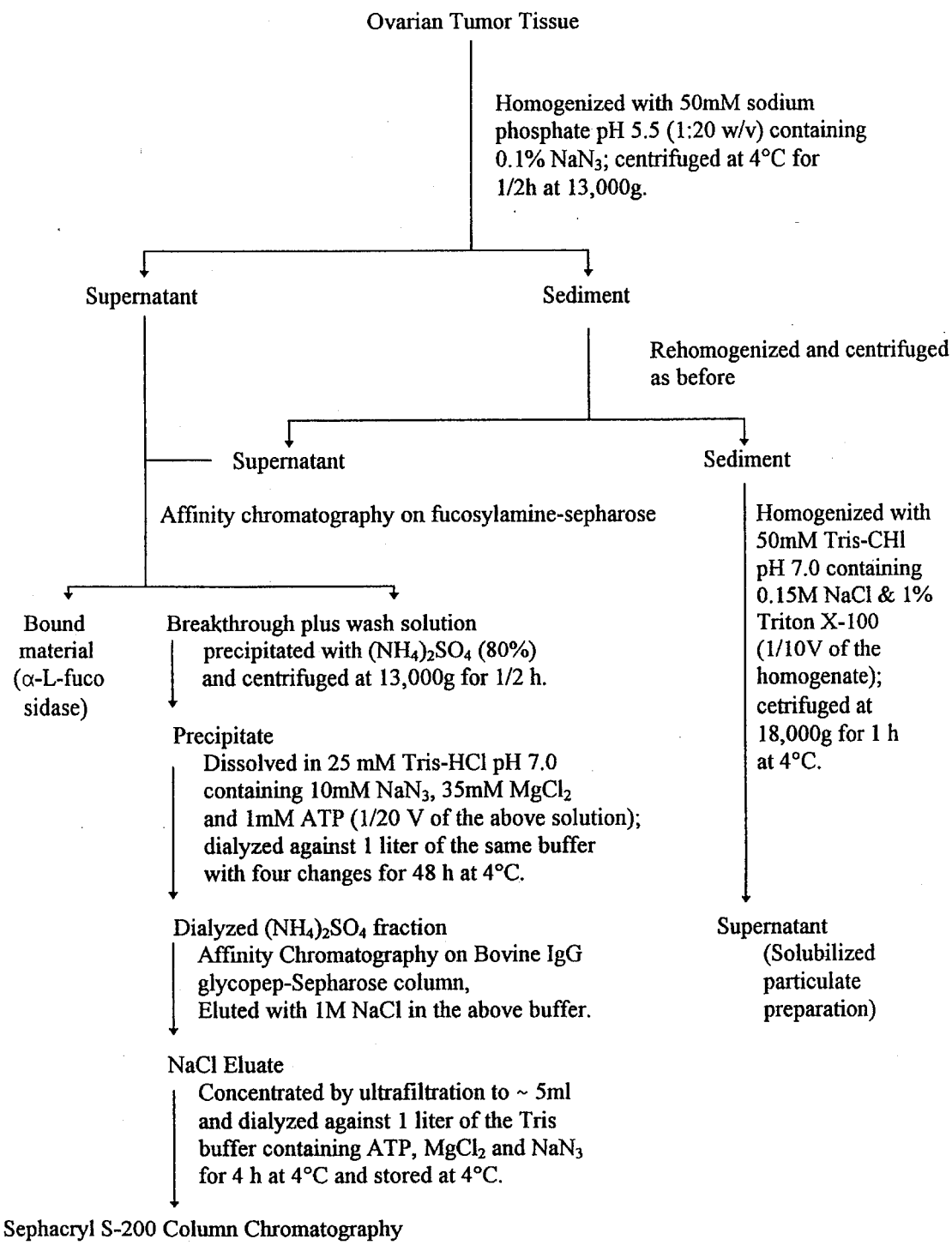
FIG. 2 The scheme for the preparation of the particulate and soluble fractions of human ovarian tumor.
Figure 3:
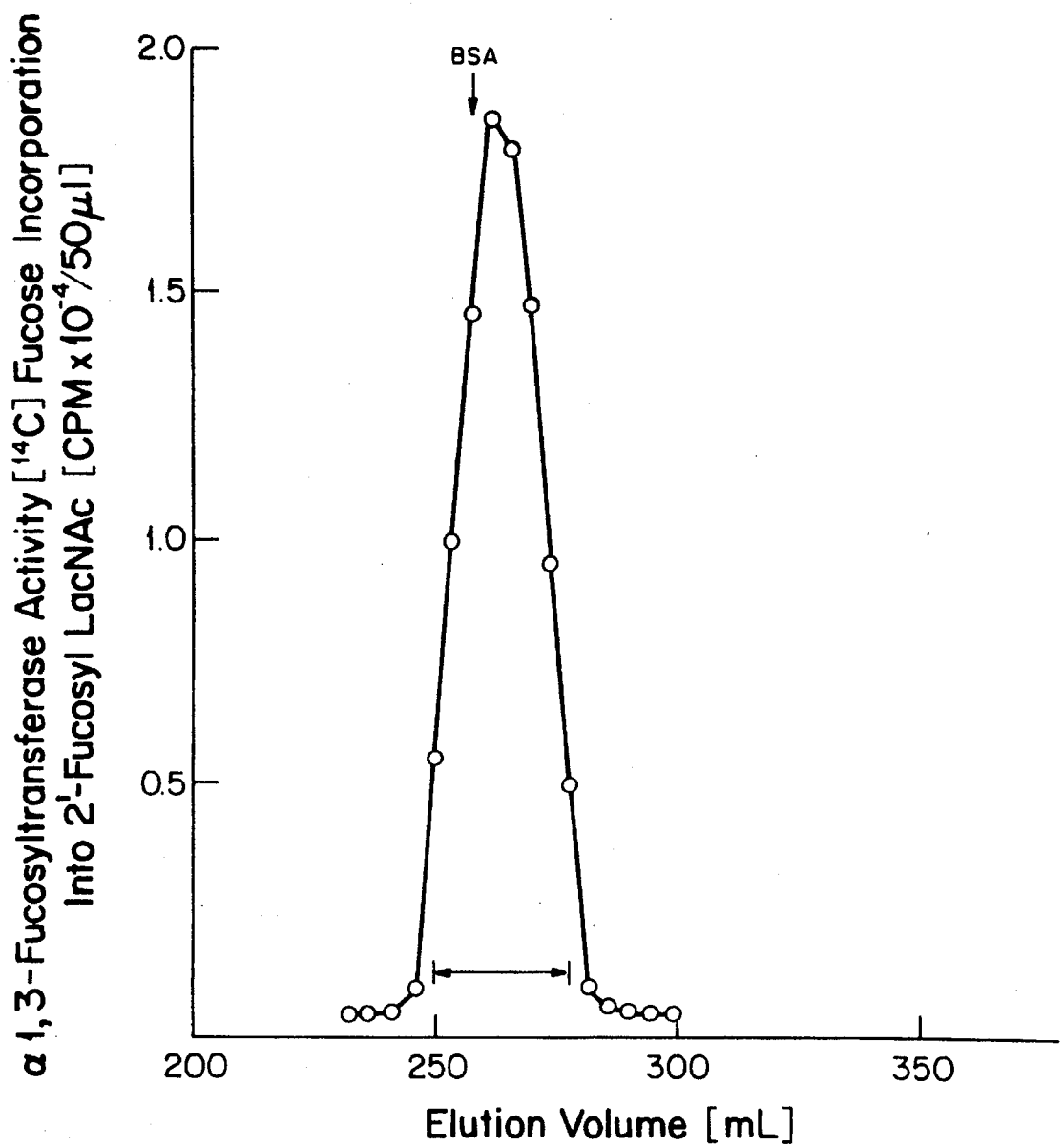
FIG. 3 Purification of α1,3-L-fucosyltransferase on Sephacryl S-200 column.

Purification of α1,3-L-Fucosyltransferase From the Soluble Fraction of Human Ovarian Tumor As shown in the scheme set forth in FIG. 2, the α-L-fucosidase-free extract of the tissue (40 g), after concentration by 80% $(NH_4)_2SO_4$ precipitation was fractionated on bovine IgG glycopep-Sepharose in batches of 25 ml. After washing the column with the equilibration buffer, the bound enzyme was eluted with 1 M NaCl in the same buffer. The protein positive fractions were pooled and processed as shown in the scheme 2.0 ml of the above preparation was loaded on a Sephacryl S-200 column (Superfine:2.6 cm×88.0 cm) equilibrated at 4° C. with 50 mM Tris-HC1, pH 7.0 containing 0.15M NaCl and 0.1% Triton X-100 and eluted with the same buffer. Fractions of 3.0 ml were collected. The fucosyltransferase activity was located in the effluent fractions, by assaying first every 5th fraction and then obtaining the activity profile by assaying the alternate fractions in that range, using 2'-fucosyl LacNAc as the acceptor. FIG. 3 shows the elution profile of α1,3-fucosyltransferase from the column. Its elution position, which is slightly later than BSA, run separately on the same column, indicates its molecular weight as <67,000 daltons. When subjected to SDS-polyacrylamide gel electrophoresis (Phast Gel 8–25, Pharmacia apparatus) the preparation showed a single diffuse band (stained by Coomassie blue) with Mr =<67,000 (FIG. 4). Table II presents the results on the purification of the enzyme. The enzyme has been purified 66 fold over the soluble extract with a recovery of 6.2%. The enzyme at this stage lost its activity either kept frozen at –20° C. or left at 4° C. for more than a week. However, the enzyme at the end of the previous step was fairly stable for at least two months at 4° C. So this preparation of enzyme was used in acceptor ability comparison studies.

3'-Sulfo LacNAc, a unique substrate for α1,3 Fucosyltransferase

The superiority of 3'-sulfo LacNAc over 2'-methyl LacNAc as the substrate for measuring serum α1,3 fucosyltransferase was tested in three different ways. First, the incubation mixtures in duplicate contained 0.3 mM 3'-sulfo LacNAc and varying amounts of 2'-methyl LacNAc (0 to 7.5 mM); the incorporation of [$^{14}$C] fucose by the serum enzyme into both substrates was measured (Table III). The incorporation of [$^{14}$C] fucose into 3'-sulfo LacNAc decreased and into 2'-methyl LacNAc increased with the increase in the concentration of the latter. The highest concentration of 2'-methyl LacNAc used in the experiment (7.5 mM) was able to bring about only 43% inhibition of the [$^{14}$C] fucose incorporation into 3'-sulfo LacNAc, whose concentration was only 0.3 mM ie. 25 fold less than 2' methyl LacNAc. Secondly, the incubation mixtures in duplicate contained 3.0 mM 2'-methyl LacNAc and varying amounts of 3'-sulfo LacNAc (0 to 0.75 mM); the incorporation of [$^{14}$C] fucose by the same serum enzyme into both substrates was measured (Table III). The [$^{14}$C] fucose incorporation into 2'-methyl LacNAc decreased and into 3'-sulfo LacNAc increased by increasing the concentration of the latter. 3'-Sulfo LacNAc at 0.75 mM (the highest concentration used in the experiment; this concentration is 1/10 of the highest concentration of 2'-methyl LacNAc used in the previous experiment) brought about 68% inhibition of the [$^{14}$C] fucose incorporation into 2'-methyl LacNAc, whose concentration was 3.0 mM, which was 4 times the amount of 3'-sulfo LacNAc. Thirdly, both 2'-methyl LacNAc and 3'-sulfo LacNAc at 0.3 mM concentration were incubated separately in duplicates with six ovarian cancer sera and one normal serum; the incorporation of [$^{14}$C] fucose into these acceptors were quantitated (Table IV). The [$^{14}$C] fucose incorporation into 3'-sulfo LacNAc was consistently higher (4–5 fold) than that into 2'-methyl LacNAc, including the assay of the normal serum. As compared to the normal serum, the cancer sera showed higher α1,3 fucosyltransferase activity in the range 176%–434% when measured with 2'-methyl LacNAc and 200%–636% with 3'-suflo LacNAc. These data thus establish the consistency and superiority of 3'-sulfo LacNAc as the substrate for measuring the level of serum α1,3-fucosyltransferase. The Km value calculated for 2'-methyl LacNAc in presence of 0.3 mM 3'-sulfo LacNAc (see Table III) was 6.67 mM and for 3'-sulfo LacNAc in presence of 3.0 mM 2'-methyl LacNAc (Table III) was 0.12 mM. These values indicate that 3'-sulfo LacNAc is a very high affinity acceptor for α1,3 fucosyltransferase. The [$^{14}$C] fucosylated product arising from 3'-sulfo LacNAc has been tentatively identified as 3'-sulfo, 3-fucosyl LacNAc by comparing strictly its mobility on paper with the synthetic authentic compound 3'-sulfo, 3-fucosyl LacNAc (see FIG. 5).

Ovarian Cancer Serum α1,3-Fucosyltransferase Activity With Various Synthetic Acceptors (see Table V)

The activity of serum α1,3-fucosyltransferase was measured with the specific substrate 2'-methyl LacNAc and compared with the ability of several other synthetic substrates to act as an acceptor of fucose. LacNAc and Galβ1,3GlcNAc were respectively 93.4% and 13.1% active suggesting that α1,3-fucosyltransferase is the dominant fucosyltransferase (>90%) in the ovarian cancer serum of the present investigation. This finding was further substantiated by the data that the β-benzyl glycosides of 2'-methyl LacNAc and LacNAc were equally active (307.9% and 358.8% respectively) whereas the same glycoside of Galβ1,3GlcNAc showed only 21.7% activity. The transfer of fucose to C-3 of GlcNAc was evident from the results that 2'-fucosyl LacNAc acted as a very good substrate (253% active) whereas 3-fucosyl LacNAc was almost inactive (only 4.7% active). Similar to the observation on the β-benzyl glycosides of LacNAc and 2'-methyl LacNAc, the β-benzyl glycoside of 2'-fucosyl LacNAc was a more effective substrate (425.0%) than the parent compound (253.1%).

When the structure of the acceptor 2'-methyl LacNAc was modified by replacing the methyl group with sulfate group in C-2', 3', 6' or 6 position and tested their ability to act as the acceptor of fucose, the following novel findings emerged. 3'-Sulfo LacNAc was the most active acceptor (340.8%) as compared to other sulfated derivatives and the non-sulfated acceptors such as 2'-methyl LacNAc and 2'-fucosyl LacNAc. Among the other sulfated derivatives, 6-sulfo LacNAc was considerably active (172.4%) and 2' and 6'-sulfo compounds were less active (22.0% and 36.2% respectively). The β-benzyl glycoside of 3' sulfo LacNAc was quite active (168.4%) but less than the parent compound. It is thus evident from the present study that β-benzylation causes an increase of 2–3 fold in the activity of non-sulfated LacNAc derivatives but, a decrease of 50% in the activity of sulfated LacNAc, (i.e., to 170% compared to 2' methyl LacNAc at 100% standard) 3-Sulfo Galβ1,3GlcNAcβ-O-Bn did not show any activity, thus implying the absence of α1,4-fucosyltransferase activity in this serum.

Ovarian Tumor Soluble Fraction α1,3-fucosyltransferase

When α1,3-fucosyltransferase activity of the partially purified enzyme preparation from the soluble portion of ovarian tumor was measured and compared with the activity of other acceptors, the following results were obtained. 2'-methyl LacNAc, LacNAc and Galβ1, 3GlcNAc were respectively 100.0%, 60.6% and 565.5% active, indicating the presence of both α1,3 and α1,4 fucosyltransferase activities in this preparation. As anticipated, the β-benzyl glycosides of the above acceptors were more active than the corresponding parent compound; in particular, the β-benzyl glycoside of Galβ1,3GlcNAc was about twice as active as Galβ1,3GlcNAc (1004.5% and 565.5% respectively). In contrast to the serum enzyme, which showed over 2-fold increase in activity with β-benzyl glycoside of 2'-methyl LacNAC (307.9% active), only a small increase was seen with the enzyme of the soluble tumor fraction (113.2%), 2'-fucosyl LacNAc and its β-benzyl glycoside were 436.1% and 373.0% active respectively whereas 3-fucosyl LacNAc was almost inactive (only 1.9% active), thus indicating the transfer of Fuc to C-3 of GlcNAc.

Among the sulfated derivatives of LacNAc, 3'-sulfo LacNAc was the most active acceptor (447.1%) followed by 6-sulfo LacNAc (272.6%) and 2' sulfo-LacNAc (32.7%). 6-'-sulfo LacNAc was the least active acceptor (5.3%). Both 3'-sulfo and 6-sulfo LacNAc showed more activity with the tumor enzyme as compared to the serum enzyme (447.1% and 272.6% compared to 340.8% and 172.4% respectively). As observed with the serum enzyme, the β-benzyl glycoside of 3'-sulfo LacNAc was less active than the parent compound towards the soluble tumor enzyme. The acceptor 3-sulfo Galβ1,3GlcNAcβ-O-Bn was highly active (415.4%) as expected since this preparation contained α1,4-fucosyltransferase activity, as noted earlier when the acceptors Galβ1,3GlcNAc and its β-benzyl glycoside were used. α1,3-L-Fucosyltransferase associated with the particular fraction of the ovarian tumor (see Table V):

The particulate enzyme was less active with LacNAc (61.8%) and Ga1β1,3GlcNAc (34.2%) indicating the major fucosyltransferase as α1,3 (>60%) in this fraction. This finding is quite different from what we found with the soluble fraction, where α1,4-fucosyltransferase activity seems to be greater than α1,3-fucosyltransferase activity. In contrast to the enzyme of the soluble fraction, which showed 436.1% activity with 2'-fucosyl LacNAc, the particulate enzyme was only 144.7% active, thus illustrating the difference in the catalytic ability of the above enzymes. The different nature of the above enzymes was made further clear, when sulfated derivatives of LacNAc was tested as acceptors. When 3'-sulfo LacNAc was found to be a highly active acceptor with the enzymes of the soluble fraction (447.1%) as well as the serum (340.8%), the particulate enzyme showed only 39% activity. As with other enzyme sources, the β-benzyl glycoside of 3'-sulfo LacNAc was less active (33.3%) than the parent compound with the particulate enzyme. Even the other sulfated derivatives exhibited differences in their affinity towards these enzymes from the tumor. When 3'-sulfo LacNAc was the most active sulfated acceptor with the enzyme of soluble fraction, 6'-sulfo and 6-sulfo LacNAc were more active (42.6% and 53.3%) than 3'-sulfo LacNAc (39.0%) and 2'-sulfo LacNAc was the least active (9.8%) with the particulate enzyme. The particulate enzyme showed very low activity (2.9%) with 3-sulfo Ga1β1,3GlcNAcβ-O-Bn in contrast to the soluble fraction, indicating that α1,4-fucosyltransferase activity was almost absent in the particulate extract.

The forgoing examples demonstrate that 3'-sulfo LacNAc can distinguish the α1,3-L-fucosyltransferase of the ovarian tumor particulate fraction from that of the soluble fraction. These enzymes show extreme difference of activities toward this substrate in comparison to 2'-methyl LacNAc. 3'-Sulfo LacNAc was 447% and 39% active respectively with soluble and particulate fractions of the ovarian tumor; in this respect, the serum enzyme resembled the soluble tumor fraction (340% active with 3'-sulfo-LacNAc).

The compounds of the invention also have biological activity with respect to proteins which mimic α1,3-L-fucosyltransferase at least insofar as such compounds of the invention will bind to both.

To show such activity, sodium 3'-O-sulfo-N-acetyllactosamine β1-OH (SE-3Galβ1–4 GLcNAcβ1) was tested for inhibition of HIV virus.

TABLE I

PROPOSED $^{13}$C-N.M.R. AND m/z[a]

| Residue | Compound | C-1 | C-2 | C-3 | C-4 |
|---|---|---|---|---|---|
| 6-O—SO$_3$Na-α-D—GlcNAc | | 93.47 | 56.41 | 72.11 | 80.76 |
| 6-O—SO$_3$Na-β-D—GlcNAc | 1 | 97.78 | 58.98 | 75.18 | 80.45 |

TABLE I-continued

PROPOSED ¹³C-N.M.R. AND m/z[a]

| Residue | | | | | |
|---|---|---|---|---|---|
| β-D—Gal (1→4) | | 105.41 | 71.47 | 75.36 | 71.14 |
| α-D—GlcNAc | | 93.48 | 56.66 | 72.06 | 81.48 |
| β-D—GlcNAc | 4 | 97.81 | 59.20 | 75.36 | 81.87 |
| 3-O—SO₃Naβ-D—Gal1→4β | | 105.49 | 71.31 | 82.98 | 69.81 |
| 3-O—SO₃Naβ-D—Gal1→4α | | 105.45 | — | — | — |
| α-D—GlcNAc | | 93.92 | 56.94 | 74.03 | 77.64 |
| β-D—GlcNAc | | 97.53 | 59.77 | 77.41 | 78.16 |
| α-L—Fuc (1→3) | 5 | 101.37 | 70.52 | 71.95 | 74.74 |
| S—O—SO₃Na-β-D—Gal (1→4) | | 104.30 | 72.11 | 83.02 | 69.52 |
| α-GlcNAc | | 93.88 | 56.89 | 74.01 | 77.78 |
| β-GlcNAc | | 97.52 | 59.77 | 77.72 | 78.26 |
| α-L—Fuc (1→3) | 10 | 101.39 | 70.54 | 71.16 | 74.73 |
| β-D—Gal (1→4) | | 104.63 | 72.10 | 75.29 | 70.52 |

| Residue | C-5 | C-6 | NAc/OMe | m/z |
|---|---|---|---|---|
| 6-O—SO₃Na-α-D—GlcNAC | 73.85 | 69.36 | 24.76 | 485.9 [M + 1]⁺, |
| 6-O—SO₃Na-β-D—GlcNAc | 75.48 | 69.30 | 25.04 | 507.9 [M + Na]⁺, |
| β-D—Gal (1→4) | 78.17 | 63.86 | — | 462.2 [M − Na]⁻ |
| α-D—GlcNAc | 72.20 | 62.97 | 24.87 | 507.9 [M + Na]⁺, |
| β-D—GlcNAc | 77.84 | 63.09 | 25.14 | 462.1 [M − Na]⁻ |
| 3-O—SO₃Naβ-D—Gal1→4β | 77.74 | 63.82 | — | |
| 3-O—SO₃Naβ-D—Gal1→4α | — | — | | |
| α-D—GlcNAc | 72.05 | 62.48 | 24.85 | 654.2 [M + Na]⁺, |
| β-D—GlcNAc | 75.51 | 62.57 | 25.10 | 608.3 [M − Na]⁻ |
| α-L—Fuc (1→3) | 69.43 | 18.09 | — | |
| S—O—SO₃Na-β-D—Gal (1→4) | 76.27 | 64.15 | — | |
| α-GlcNAc | 72.05 | 62.53 | 24.81 | |
| β-GlcNAc | 75.64 | 62.62 | 25.06 | 530.1 [M + 1]⁺, |
| α-L—Fuc (1→3) | 69.47 | 18.09 | — | 552.0 [M + Na]⁺ |
| β-D—Gal (1→4) | 76.15 | 64.30 | — | |

[a]All compounds gave satisfactory elemental analysis.

TABLE II

PARTIAL PURIFICATION OF α1,3-L-FUCOSYLTRANSFERASE FROM THE SOLUBLE FRACTION OF HUMAN OVARIAN TUMOR

| | α1,3-L-Fucosyltransferase Activity (¹⁴C) Fucose (CPM) Incorporated into 2'-Fucosyl N-acetyllactosamine | | | |
|---|---|---|---|---|
| Fraction | Activity/mg protein CPM × 10⁻⁵ | Total Activity CPM × 10⁻⁶ | Purification (fold) | Recovery (%) |
| Ovarian Tumor Soluble Fraction Depleted of α-L-Fucosidase | 0.500 | 40.00 | 1.0 | 100.0 |
| Precipitation with 80% Ammonium Sulfate | 0.719 | 35.95 | 1.4 | 89.9 |
| Affinity Chromatography on Bovine IgG Glycopeptide-Sepharose Column | 7.782 | 15.56 | 15.6 | 38.9 |
| Chromatography on Sephacryl S-200 Column | 33.100 | 2.46 | 66.2 | 6.2 |

TABLE III

THE ACCEPTOR ABILITY OF 3'-SULFO LacNAc IN PRESENCE OF THE COMPETITIVE SUBSTRATE 2'-METHYL LacNAc AND VICE VERSA WITH OVARIAN CANCER SERA AS THE SOURCE OF α1,3-L-FUCOSYLTRANSFERASE

| Conc. of the Competitive Substrate (mM) | | Incorporation of [¹⁴C] Fucose (CPM) | |
|---|---|---|---|
| 2'-Methyl LacNAc | 3'-Sulfo LacNAc* (0.3 mM) | | 2'-Methyl LacNAc |
| 0 | 2520 | | 157 |
| 1.5 | 2132 | | 1143 |
| 3.0 | 1872 | | 1614 |
| 4.5 | 1748 | | 1973 |
| 6.0 | 1712 | | 2698 |
| 7.5 | 1428 | | 2788 |
| 3'-Sulfo LacNAc | 2'-Methyl LacNAc | | 3'-Sulfo LacNAc |
| 0 | 3664 | | 140 |
| 0.15 | 2581 | | 1294 |
| 0.30 | 2191 | | 2181 |
| 0.45 | 1737 | | 2417 |
| 0.65 | 1184 | | 2373 |
| 0.75 | 1187 | | 2560 |

*There was no inhibition by 2'-methyl LacNAc, when 3'-sulfo LacNAc was present at 3.0 mM concentration. The Km value calculated for 2'-methyl LacNAc in presence of 0.3 mM 3'-sulfo LacNAc was 6.67 mM and that for 3'-sulfo LacNAc in presence of 3.0 mM 2'-methyl LacNAc was 0.12 mM.

TABLE IV

THE UTILITY OF 3'-SULFO LacNAc AS A HIGHLY SENSITIVE ACCEPTOR FOR THE DETECTION OF SERUM α1,3-L-FUCOSYLTRANSFERASE

| | Incorporation of [$^{14}$c] Fucose (CPM) into the Acceptor (0.30 mM) | | |
|---|---|---|---|
| | 2'-Methyl LacNac A | 3'-Sulfo LacNAc B | Ratio B/A |
| Ovarian Cancer Sera: | | | |
| 1 | 1325 (334) | 7310 (474) | 5.52 |
| 2 | 1724 (434) | 9816 (636) | 6.69 |
| 3 | 1359 (342) | 5261 (341) | 3.87 |
| 4 | 1347 (339) | 5480 (355) | 4.06 |
| 5 | 699 (176) | 3088 (200) | 4.42 |
| 6 | 975 (246) | 5483 (355) | 5.62 |
| Normal Serum | 397 | 1543 | 3.89 |

The values in parentheses are the percentage of the ratio between the CPM obtained for cancer serum and normal serum.

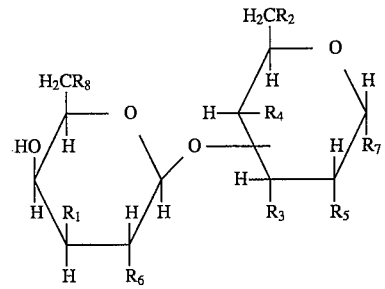

wherein at least one of $R_1$ and $R_2$ is sulfate, one of $R_3$ and $R_4$ represents the link to the linking oxygen atom and the remaining $R_1$–$R_8$ groups are selected from —OH, -$OR_9$ or -$R_{10}$ where $R_9$ and $R_{10}$ are independently selected from the group consisting of lower alkyl, lower alkenyl, allyl, phenyl, benzyl, monosaccharides, oligosaccharides, toxins, antibodies, enzymes, amino acids and amino acid chains and wherein $R_{10}$ may further be ester, ether, amino or fluoro; provided that, at least three of the remaining $R_1$–$R_8$ groups are —OH.

TABLE V

DIFFERENTIATION OF THE DISTINCT SPECIFICITIES OF OVARIAN CANCER α1,3-L-FUCOSYLTRANSFERASES PRESENT IN THE PARTICULATE AND SOLUBLE FRACTIONS BY USING SYNTHETIC SUBSTRATES

| | Source of α1,3-L-Fucosyltransferase | | | | | |
|---|---|---|---|---|---|---|
| | Ovarian Cancer Sera | | Ovarian Tumor | | | |
| | | | Soluble Fraction | | Particulate Fraction | |
| Carbohydrate Acceptor | [$^{14}$C] Fucose Incorporated (CPM) | Relative Percent | [$^{14}$C] Fucose Incorporated (CPM) | Relative Percent | [$^{14}$C] Fucose Incorporated (CPM) | Relative Percent |
| 2'-methyl LacNAc | 1730 | 100 | 7392 | 100 | 48252 | 100 |
| 2'-methyl LacNAcβ-O—Bn | 5326 | 307.9 | 8367 | 113.2 | 71989 | 149.2 |
| LacNAc | 1615 | 93.4 | 4480 | 60.6 | 29842 | 61.8 |
| LacNAcβ-O—Bn | 6207 | 358.8 | 8249 | 111.6 | 64223 | 132.9 |
| LacNAcβ1,3Galβ-O—PNP | 2886 | 166.8 | 6432 | 87.0 | 33759 | 70.0 |
| 2'-Sulfo LacNAc | 380 | 22.0 | 2414 | 32.7 | 4718 | 9.8 |
| 6'-Sulfo LacNAc | 626 | 36.2 | 395 | 5.3 | 20543 | 42.6 |
| 6-Sulfo LacNAc | 2983 | 172.4 | 20148 | 272.6 | 25740 | 53.3 |
| 3-Fucosyl LacNAc | 82 | 4.7 | 144 | 1.9 | 1801 | 3.7 |
| 2'-Fucosyl LacNAc | 4379 | 253.1 | 32235 | 436.1 | 69824 | 144.7 |
| 2'-Fucosyl LacNAcβ-O—Bn | 7352 | 425.0 | 27571 | 373.0 | 83975 | 174.0 |
| 3'-Sulfo-LacNAc | 5894 | 340.8 | 33049 | 447.1 | 18793 | 39.0 |
| 3'-Sulfo LacNAcβ-O—Bn | 2913 | 168.4 | 13585 | 183.8 | 16062 | 33.3 |
| 3-SulfoGalβ1,3G1cNAcβ-O—Bn | 0 | 0 | 30704 | 415.4 | 1382 | 2.9 |
| GlcNAcβ1,6GalNAcα-O—ONp | 164 | 9.5 | 0 | 0 | | |
| Galβ1,3G1cNAc | 227 | 13.1 | 41802 | 565.5 | 16511 | 34.2 |
| Galβ1,3G1cNAcβ-O—Bn | 376 | 21.7 | 74260 | 1004.5 | 18221 | 37.8 |
| Galβ1,3G1cNAcβ1,3Galβ-O—Me | 739 | 42.7 | | | 20559 | 42.6 |

What is claimed is:

1. An oligosaccharide having at least two saccharide rings and 3' and 6 position carbon atoms and containing at least one sulfate group bound to at least one of the 3' or 6 carbon atoms which oligosaccharide binds to α1,3-L-fucosyltransferase enzyme with higher affinity than 2'-methyl N-acetyllactosamine binds to said enzyme.

2. The oligosaccharide of claim 1 represented by the formula:

3. The oligosaccharide of claim 2 wherein $R_5$ or $R_7$ is a saccharide selected from the group consisting of glucose, fructose, aldose, mannose, ribose and galactose.

4. The oligosaccharide of claim 2 wherein $R_1$ is $Na^+$—$O_3SO$—; $R_2$ is —OH; $R_3$ is —OH; $R_4$ is the bond to the ether oxygen; $R_5$ is N-acetylamino; $R_6$ is —OH; $R_7$ is —OH, nitrophenyl or benzyl; $R_8$ is —OH and $R_9$ is —OH.

5. The oligosaccharide of claim 2 wherein $R_1$ is $Na^+$—$O_3SO$—; $R_2$ is —OH; $R_3$ is the bond to the ether oxygen; $R_4$ is —OH; $R_5$ is N-acetylamino; $R_6$ is —OH; $R_7$ is —OH, nitrophenyl or benzyl; $R_8$ is —OH and $R_9$ is —OH.

6. The oligosaccharide of claim 2 wherein $R_1$ is —OH; $R_2$ is $Na^+$—$O_3SO$—; $R_3$ is —OH; $R_4$ is the bond to the ether oxygen; $R_5$ is N-acetylamino; $R_6$ is —OH; $R_7$ is —OH, nitrophenyl or benzyl; $R_8$ is —OH and $R_9$ is —OH.

7. The oligosaccharide of claim 2 wherein $R_1$ is —OH; $R_2$ is $Na^+$—$O_3SO$—; $R_3$ is the bond to the ether oxygen; $R_4$ is —OH; $R_5$ is N-acetylamino; $R_6$ is —OH; $R_7$ is —OH nitrophenyl or benzyl; $R_8$ is —OH and $R_9$ is —OH.

8. The oligosaccharide of claim 2 wherein $R_1$ is a sulfate group.

9. The oligosaccharide of claim 2 wherein $R_2$ is a sulfate group.

10. The oligosaccharide of claim 2 wherein $R_5$ is N-acetylamino.

11. The oligosaccharide of claim 2 wherein $R_7$ is —$OR_9$ where $R_9$ is paranitrophenyl.

12. The oligosaccharide of claim 2 wherein $R_7$ is —$OR_9$ where $R_9$ is benzyl.

13. The oligosaccharide of claim 2 wherein $R_7$ is —$OR_9$ where $R_9$ is paranitrobenzyl.

14. A method for analyzing for the presence of $\alpha 1,3$-L-fucosyltransferase enzyme which comprises contacting a sample containing fucosyltransferase with the compound of claim 1 to form a complex between the fucosyltransferase and said compound and detecting the fucosyltransferase combined with said compound.

15. A method for analyzing the presence of $\alpha 1,3$-L-fucosyltransferase enzyme which comprises contacting a sample containing fucosyltransferase with the compound of claim 2 to form a complex between the fucosyltransferase and said compound and detecting the fucosyltransferase combined with said compound.

16. A method for analyzing the presence of $\alpha 1,3$-L-fucosyltransferase enzyme which comprises contacting a sample containing fucosyltransferase with the compound of claim 3 to form a complex between the fucosyltransferase and said compound and detecting the fucosyltransferase combined with said compound.

17. A method for analyzing the presence of $\alpha 1,3$-L-fucosyltransferase enzyme which comprises contacting a sample containing fucosyltransferase with the compound of claim 4 to form a complex between the fucosyltransferase and said compound and detecting the fucosyltransferase combined with said compound.

18. A method for analyzing the presence of $\alpha 1,3$-L-fucosyltransferase enzyme which comprises contacting a sample containing fucosyltransferase with the compound of claim 5 to form a complex between the fucosyltransferase and said compound and detecting the fucosyltransferase combined with said compound.

19. A method for analyzing the presence of $\alpha 1,3$-L-fucosyltransferase enzyme which comprises contacting a sample containing fucosyltransferase with the compound of claim 6 to form a complex between the fucosyltransferase and said compound and detecting the fucosyltransferase combined with said compound.

20. A method for analyzing the presence of $\alpha 1,3$-L-fucosyltransferase enzyme which comprises contacting a sample containing fucosyltransferase with the compound of claim 7 to form a complex between the fucosyltransferase and said compound and detecting the fucosyltransferase combined with said compound.

21. A method for analyzing the presence of $\alpha 1,3$-L-fucosyltransferase enzyme which comprises contacting a sample containing fucosyltransferase with the compound of claim 8 to form a complex between the fucosyltransferase and said compound and detecting the fucosyltransferase combined with said compound.

22. A method for analyzing the presence of $\alpha 1,3$-L-fucosyltransferase enzyme which comprises contacting a sample containing fucosyltransferase with the compound of claim 9 to form a complex between the fucosyltransferase and said compound and detecting the fucosyltransferase combined with said compound.

23. A method for analyzing the presence of $\alpha 1,3$-L-fucosyltransferase enzyme which comprises contacting a sample containing fucosyltransferase with the compound of claim 10 to form a complex between the fucosyltransferase and said compound and detecting the fucosyltransferase combined with said compound.

24. A method for analyzing the presence of $\alpha 1,3$-L-fucosyltransferase enzyme which comprises contacting a sample containing fucosyltransferase with the compound of claim 11 to form a complex between the fucosyltransferase and said compound and detecting the fucosyltransferase combined with said compound.

25. A method for analyzing the presence of $\alpha 1,3$-L-fucosyltransferase enzyme which comprises contacting a sample containing fucosyltransferase with the compound of claim 12 to form a complex between the fucosyltransferase and said compound and detecting the fucosyltransferase combined with said compound.

26. A method for analyzing the presence of $\alpha 1,3$-L-fucosyltransferase enzyme which comprises contacting a sample containing fucosyltransferase with the compound of claim 13 to form a complex between the fucosyltransferase and said compound and detecting the fucosyltransferase combined with said compound.

27. A method for inhibiting the biological activity of $\alpha 1,3$-L-fucosyltransferase which comprises binding the $\alpha 1,3$-L- fucosyltransferase to a compound of claim 1.

28. A method for inhibiting the biological activity of $\alpha 1,3$-L-fucosyltransferase which comprises binding the $\alpha 1,3$-L- fucosyltransferase to a compound of claim 2.

29. A method for inhibiting the biological activity of $\alpha 1,3$-L-fucosyltransferase which comprises binding the $\alpha 1,3$-L- fucosyltransferase to a compound of claim 3.

30. A method for inhibiting the biological activity of $\alpha 1,3$-L-fucosyltransferase which comprises binding the $\alpha 1,3$-L- fucosyltransferase to a compound of claim 4.

31. A method for inhibiting the biological activity of $\alpha 1,3$-L-fucosyltransferase which comprises binding the $\alpha 1,3$-L- fucosyltransferase to a compound of claim 5.

32. A method for inhibiting the biological activity of $\alpha 1,3$-L-fucosyltransferase which comprises binding the $\alpha 1,3$-L- fucosyltransferase to a compound of claim 6.

33. A method for inhibiting the biological activity of $\alpha 1,3$-L-fucosyltransferase which comprises binding the $\alpha 1,3$-L- fucosyltransferase to a compound of claim 7.

34. A method for inhibiting the biological activity of $\alpha 1,3$-L-fucosyltransferase which comprises binding the $\alpha 1,3$-L- fucosyltransferase to a compound of claim 8.

35. A method for inhibiting the biological activity of $\alpha 1,3$-L-fucosyltransferase which comprises binding the $\alpha 1,3$-L- fucosyltransferase to a compound of claim 9.

36. A method for inhibiting the biological activity of $\alpha 1,3$-L-fucosyltransferase which comprises binding the $\alpha 1,3$-L- fucosyltransferase to a compound of claim 10.

37. A method for inhibiting the biological activity of $\alpha 1,3$-L-fucosyltransferase which comprises binding the $\alpha 1,3$-L- fucosyltransferase to a compound of claim 11.

38. A method for inhibiting the biological activity of $\alpha 1,3$-L-fucosyltransferase which comprises binding the $\alpha 1,3$-L- fucosyltransferase to a compound of claim 12.

39. A method for inhibiting the biological activity of $\alpha 1,3$-L-fucosyltransferase which comprises binding the $\alpha 1,3$-L- fucosyltransferase to a compound of claim 13.

* * * * *

UNITED STATES PATENT AND TRADEMARK OFFICE
CERTIFICATE OF CORRECTION

PATENT NO. : 5,620,864

DATED : April 15, 1997

INVENTOR(S) : Matta et al.

It is certified that error appears in the above-indentified patent and that said Letters Patent is hereby corrected as shown below:

In Claim 4, line 1, "$Na^{+-}$" should read "$Na^{+-}$".

In Claim 5, line 1, "$Na^{+}-$" should read "$Na^{+-}$".

In Claim 6, line 2, "$Na^{+}-$" should read "$Na^{+-}$".

In Claim 7, line 2, "$Na^{+}-$" should read "$Na^{+-}$".

Signed and Sealed this

Nineteenth Day of August, 1997

Attest:

BRUCE LEHMAN

Attesting Officer

Commissioner of Patents and Trademarks